US006458929B1

(12) United States Patent
Carpén et al.

(10) Patent No.: US 6,458,929 B1
(45) Date of Patent: Oct. 1, 2002

(54) MYOTILIN, A NOVEL ACTIN-ORGANIZING PROTEIN

(75) Inventors: Olli Carpén, Espoo (FI); Mikaela Grönholm, Helsinki (FI); Leena Heiska, Helsinki (FI); Olli-Matti Mykkänen, Helsinki (FI); Paula Salmikangas, Klaukkala (FI)

(73) Assignee: Licentia Ltd., Helsinki (FI)

( * ) Notice: Subject to any disclaimer, the term of this patent is extended or adjusted under 35 U.S.C. 154(b) by 0 days.

(21) Appl. No.: 09/354,151

(22) Filed: Jul. 16, 1999

Related U.S. Application Data

(60) Provisional application No. 60/093,169, filed on Jul. 17, 1998.

(51) Int. Cl.⁷ .................. C07K 14/00; G01M 33/53
(52) U.S. Cl. .................. 530/350; 530/300; 435/7.1; 435/183
(58) Field of Search .................. 530/350, 300; 435/183, 7.1

(56) References Cited

U.S. PATENT DOCUMENTS 5,672,694 A    9/1997   Campbell et al. .......... 536/22.1

FOREIGN PATENT DOCUMENTS

WO       WO 9730085 A      8/1997

OTHER PUBLICATIONS

Hillier et al., "WashU–Merck EST Project 1997", EMBL Database Account No.: A A 460075 (Jun. 13, 1997) XP002126859.

Bubb et al., The Journal of Biological Chemistry, 269(21), pp. 14869–14871 (May 27, 1994) XP002126860.

Yamaoka et al., Neuromuscular Disord., 4(5/6) pp. 471–475 (1994) XP000857664.

Salmikangas et al., Human Molecular Genetics, 8(7), pp. 1329–1336 (Jul. 1999) XP002126861.

Salmikangas et al., EMBL Database Acc No.: AF1444777 (Jul. 20, 1999) XP002127001.

Jordan et al., Current Opinion in Cell Biology, 10, pp. 123–130 (1998).

Salmikangas et al., Molcular Biology of the Cell, vol. 9, Supp. 'S!, pp. 154–154 (Nov. 1998) XP000865833.

Bartoloni et al., Genomics 54, 250–255 (1998).

M. Gautel et al., EMBO J, 12(10):3827–34 (Oct. 1993) (Abstract).

M. Gaulet et al., Gen Bank 1997, Accession No. I38344.

S. Labeit et al., Science, vol. 270 (Oct. 13, 1995).

G. Musco et al., Biochemistry, 34, 553–561 (1995).

*Primary Examiner*—Karen Cochrane Carlson
*Assistant Examiner*—Hope Robinson
(74) *Attorney, Agent, or Firm*—Birch, Stewart, Kolasch & Birch, LLP

(57) ABSTRACT

The present invention concerns a novel cytoskeletal protein, myotilin, which contains Ig-like domains homologous to a giant sarcomeric structural protein titin. Myotilin is expressed in skeletal and cardiac muscles, it colocalizes with α-actinin in the sarcomeric I-bands and directly interacts with α-actinin. Expression of myotilin in mammalian non-muscle cells and in yeast causes reorganization of actin into thick F-actin bundles and inhibits growth of yeast cells.

6 Claims, 12 Drawing Sheets

(7 of 12 Drawing Sheet(s) Filed in Color)

| | | | | | |
|---|---|---|---|---|---|
| 1 | MFNYERPKHF | IQSQNPCGSR | LQPPGPETSS | FSSQTKQSSI | IIQPRQCTEQ | 50 |
| 51 | RFSASSTLSS | HITMSSSAFP | ASPQQHAGSN | PGQRVTTTYN | QSPASFLSSI | 100 |
| 101 | LPSQPDYNSS | KIPSAMDSNY | QQSSAGQPIN | AKPSQTANAK | PIPRTPDHEI | 150 |
| 151 | QGSKEALIQD | LERKLKCKDT | LLHNGNQRLT | YEEKMARRLL | GPQNAAAVFQ | 200 |
| 201 | AQDDSGAQDS | QQHNSEHARL | QVPTSQVRSR | STSRGDVNDQ | DAIQEKFYPP | 250 |
| 251 | RFIQVPENMS | IDEGRFCRMD | FKVSGLPAPD | VSWYLNGRTV | QSDDLHKMIV | 300 |
| 301 | SEKGLHSLIF | EVVRASDAGA | YACVAKNRAG | EATFTVQLDV | LAKEHKRAPM | 350 |
| 351 | FIYKPQSKKV | LEGDSVKLEC | QISAIPPPKL | FWKRNNEMVQ | FNTDRISLYQ | 400 |
| 401 | DNTGRVTLLI | KDVNKKDAGW | YTVSAVNEAG | VTTCNTRLDV | TARPNQTLPA | 450 |
| 451 | PKQLRVRPTF | SKYLAALNGKG | LNVKQAFNPE | GEFQRLAAQS | GLYESEEL | 498 |

FIG.1A

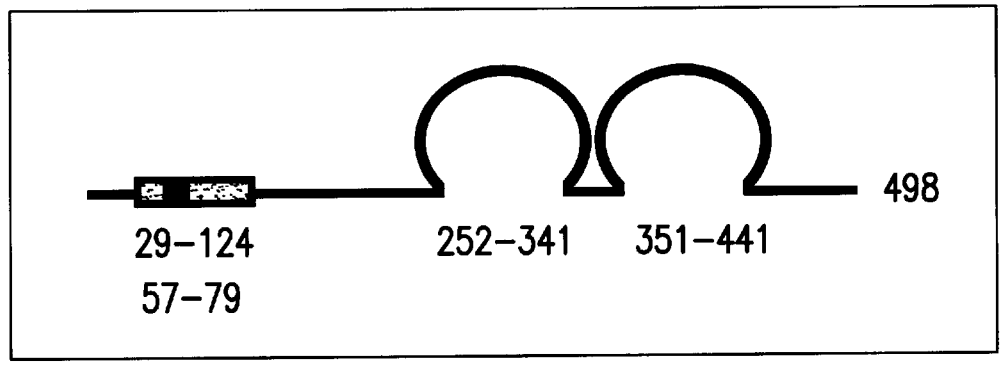

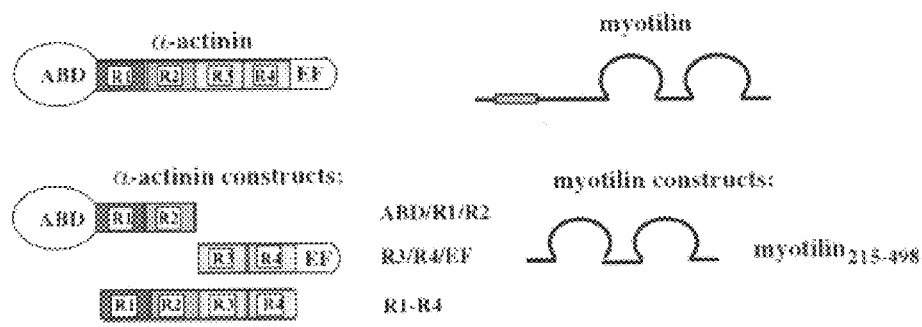
FIG.8A
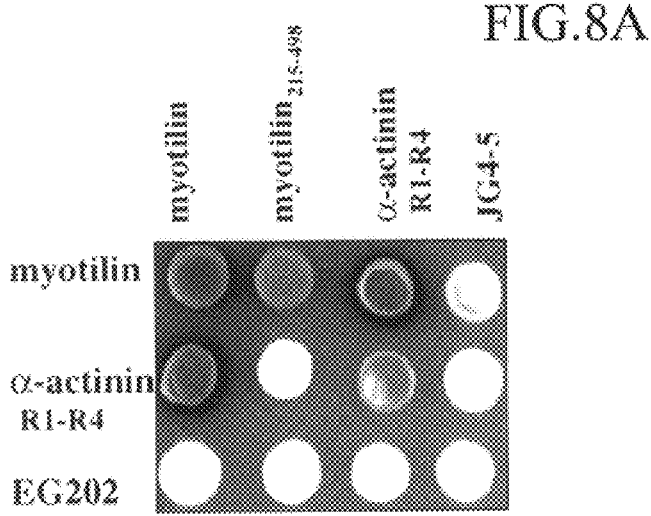
FIG.8B
FIG.8C
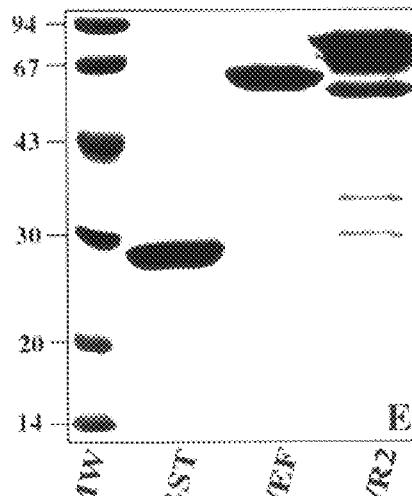
FIG.8D
FIG.8E

MYOTILIN, A NOVEL ACTIN-ORGANIZING PROTEIN

This application claims priority on provisional Application No. 60/093,169 filed on Jul. 17, 1998, the entire contents of which are hereby incorporated by reference.

FIELD OF THE INVENTION

The present invention concerns a novel cytoskeletal protein, myotilin, which contains Ig-like domains homologous to a giant sarcomeric structural protein titin. Myotilin is expressed in skeletal and cardiac muscles, it colocalizes with α-actinin in the sarcomeric I-bands and directly interacts with α-actinin. Expression of myotilin in mammalian non-muscle cells and in yeast causes reorganization of actin into thick F-actin bundles and inhibits growth of yeast cells.

BACKGROUND OF THE INVENTION

Among the various cell types in the higher organisms, the striated muscle cells have differentiated to carry out the task of force generation and transduction. To serve this very specialized function, the muscle cells express many gene products or mRNA splice variants that are not found in other cells of the body. Many of the muscle specific genes encode cytoskeletal proteins by which a highly organized sarcomeric architecture is created [1, 2]. The major components of thin and thick filaments, actin and myosin, are linked to a variety of molecules regulating the assembly, structural integrity and function of the striated muscle. For instance, the giant protein titin that spans from the M-line of the thick filament to the Z-line of the thin filament, functions as a spring and a ruler of the sarcomere, and α-actinin, an actin-binding protein, crosslinks thin filaments into antiparallel bundles in the Z-lines [2–8]. The force generated by cytoskeletal components of the contracting subunits is transduced through the plasma (sarcolemma) membrane to the extracellular matrix via a connecting multi-subunit dystrophin-glycoprotein complex [9, 10].

The importance of the individual components of the sarcomeric and sarcolemmal structures is highlighted by recent findings demonstrating that mutations in several different structural proteins result in muscular diseases such as muscular dystrophies and cardiomyopathies [9–12]. Many of the identified muscle disease genes encode proteins of dystrophin-associated sarcolemmal complex, but recently also other types of molecules, including regulators of the sarcomeric architecture, have been indicated to participate in pathogenesis of certain disease forms. A mutation in α-tropomyosin gene, TPM3, was shown to cause an autosomal dominant nemaline myopathy (NEM1) [13]. The nebulin gene is a candidate for another form of nemaline myopathy (NEM2) [14] and the titin gene is a candidate for autosomal dominant tibial muscular dystrophy [15].

In spite of recent advances, several clinically distinguishable forms of muscular dystrophy with unidentified disease genes exist. Two forms of muscular dystrophy, a dominant form of limb-girdle muscular dystrophy (LGMD1A) and a dominant form of distal myopathy with vocal cord and pharyngeal weakness (VCPMD) have been mapped to an overlapping locus in 5q31 [16,17].

Several studies have shown that actin cytoskeleton is substantially modified in transformed cells [reviewed in 18, 19 and 20]. In cells, actin molecules undergo dynamic reorganization, i.e. polymer formation from actin monomers and disruption or modulation of existing polymers. These events are controlled by a variety of actin-binding proteins with versatile activities. The complex dynamic regulation of cytoskeletal filaments depends on the expression and activity of various components within cells. Interestingly, a large fraction of actin exist in most cell types as monomers, whereas in muscle cells more than 99% of actin is in filaments. This suggests that muscle cells express protein(s), some of which may be unknown, whose function is to preserve the actin molecule equilibrium in a polymerized state. Taken the important role of actin cytoskeleton in functions related to abnormal cell growth and the changes in actin organization in transformed cells, factors regulating actin organization serve as attractive targets for cancer chemotherapy. Such an idea has been recently supported by experimental data indicating that two novel actin-stabilizing components, jasplakinolide and chondramides inhibit growth of transformed cells [20, 21].

SUMMARY OF THE INVENTION

Here we describe the cDNA sequence and structure of myotilin gene, which encodes a novel component of the striated and cardiac muscle cytoskeleton. Myotilin protein contains two C2-type Ig-like domains with considerable homology to certain Ig-domains of titin. Myotilin resides both in the sarcomere, where it localizes within the I-bands and is bound to α-actinin, and along the sarcolemmal membrane. The myotilin gene locates in chromosome 5q31 inside a 2Mb region, which contains the LGMD1A disease gene [16], and thus is a candidate for LGMD1A. Transfection of myotilin into mammalian cells and yeast cells induces formation of thick actin bundles and reduces growth of yeast, indicating a role for myotilin in organization of the actin-containing cytoskeleton.

The designation "myotilin" comes from myofibrillar protein with titin-like Ig-domains. It should be noted that the designation "myofilin" which was used earlier, was amended due to the fact that a muscle-specific gene of Echinococcus granulosus was previously termed "myophilin" [22]. Although the terms are spelled differently, a similar pronunciation creates possibility for confusion and therefore the designation "myofilin" was changed to "myotilin".

Expression of myotilin in mammalian cells and yeast causes reorganization of actin into thick filaments. The expression of myotilin or its C-terminal fragment (amino acids 215–498) changes yeast morphology and reduces growth rate. The actin-organizing and growth inhibiting properties suggest that myotilin or its fragments may be used in development of substances to control cell growth in various pathological conditions including treatment of cancer or microbial infections.

DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A. Deduced amino acid sequence of myotilin. The inferred 498 residue myotilin polypeptide is shown. Said sequence is also given in the appended Sequence listing as SEQ ID NO:2. The regions containing Ig-like domains are boxed. Dashed line indicates the 17 residue peptide used for production of rabbit antiserum. The nucleotide sequence of cDNA for myotilin has been deposited to Genbank database (accession number AF144477). The nucleotide sequence is given as SEQ ID NO:1.

FIG. 1B. Schematic structure of myotilin. Schematic diagram of the protein structure shows the serine-rich region (grey box) containing a hydrophobic stretch (black box) and the two Ig-domains (loops). The approximate positions of various regions are shown below.

FIG. 1C. Myotilin sequence comparison with titin. Two paired Ig-domains and flanking regions of human myotilin and titin (Ig-domains 7 and 8) were aligned using the Clustal W method. Residues belonging to the Ig-like domains are boxed. Black boxes indicate conserved residues and grey boxes indicate conservative substitutions. GeneBank accession number for titin is I38344 (SEQ ID NO:3).

FIGS. 8A to 8E. Homotypic interaction of myotilin and association with α-actinin. (A) Domain structure of α-actinin and myotilin and the constructs used in yeast two-hybrid and in vitro binding assays. ABD=actin-binding domain, R=spectrin-like repeat, EF=EF-hand region. The grey box in myotilin indicates the serine-rich region and the loops indicate Ig-like domains. (B) A photomicrograph of the yeast two-hybrid interactions. On the left are the expressed bait fusion proteins and on the top are the prey fusion proteins. EG202=empty bait vector and JG4-5=prey vector. Color reaction is an indicator of an interaction. (C) Quantitation of β-galactoside values. The bait and prey fusion proteins are as in B. The β-galactosidase values are categorized as follows: −=<20; +=21–150; ++=151–300; +++=301–450. (D) Affinity precipitation analysis of myotilin—α-actinin interaction. The NH$_2$-terminal and COOH-terminal parts of α-actinin were expressed as GST-fusion proteins, purified and bound to glutathione-Agarose beads. $^{35}$S-labeled in vitro translated myotilin was allowed to bind GST-α-actinin fusion protein-containing beads. Bound material was separated in SDS-PAGE and autoradiographed. Myotilin binds the R3/R4/EF construct, whereas the ABD/R1/R2 and the GST control are not binding. (E) Coomassie stained SDS-PAGE demonstrating the constructs used in the binding assay.

DETAILED DESCRIPTION OF THE INVENTION

Characterization of Myotilin cDNA

Figure 1C:
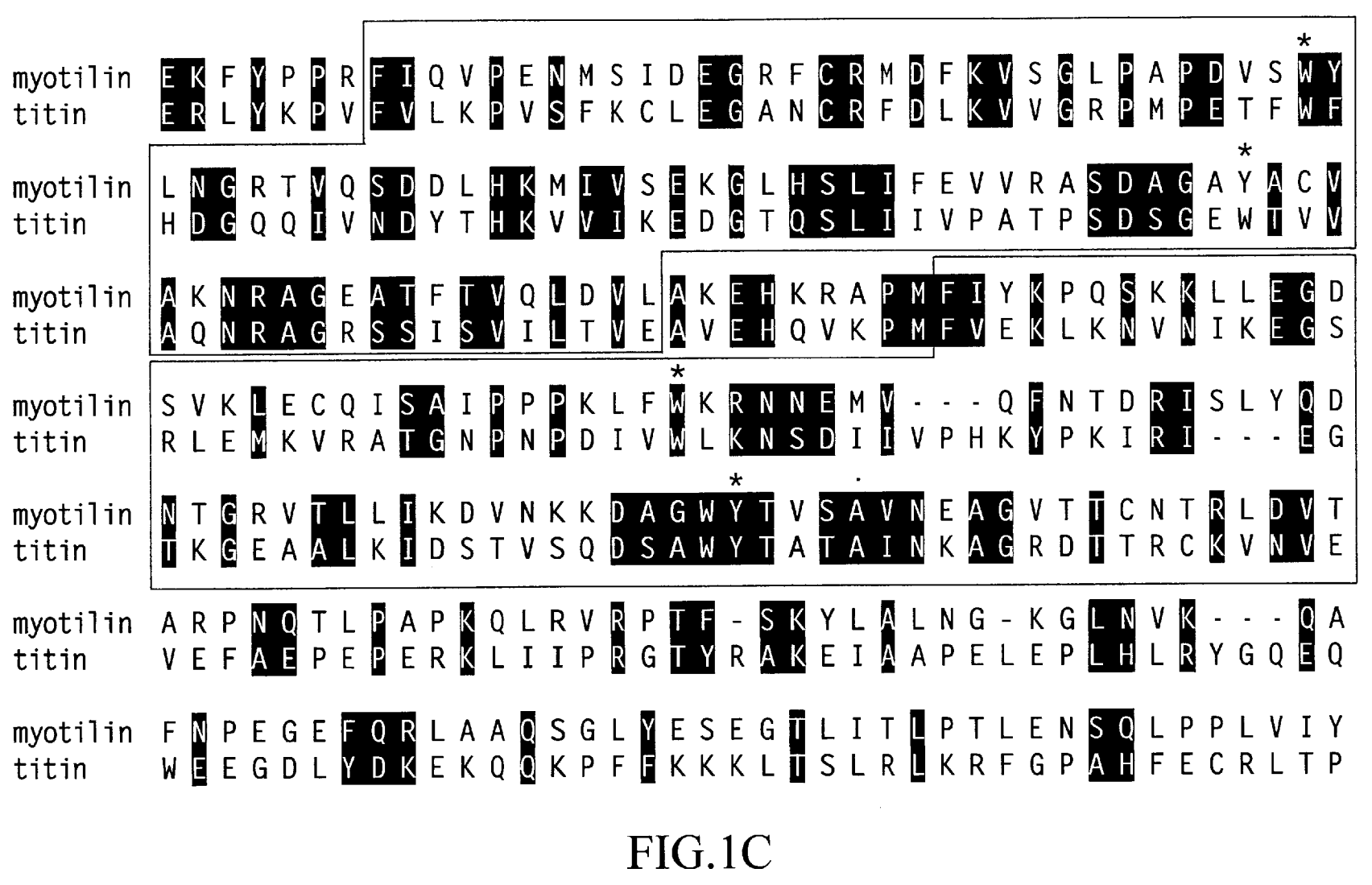

A partial cDNA encoding myotilin was initially discovered based on a yeast two-hybrid screen for novel cytoskeletal components. Using this sequence as a probe, we cloned a 2244 bp cDNA from a human skeletal muscle library. The cDNA contains a 1494 bp open reading frame (nucleotides 281 to 1774) encoding a 498 amino acid polypeptide (SEQ ID NO:2), which we have termed myotilin (FIG. 1A). The methionine start codon is in partial agreement with the Kozak consensus sequence. The NH$_2$-terminal sequence is particularly rich in serine residues often arranged in a paired fashion, and contains a 23 amino acid hydrophobic stretch (residues 57–79). Upon database searches, the NH$_2$-terminal sequence is unique and does not contain known structural domains.

The COOH-terminus of the protein is predicted to form two Ig-like domains with conserved key residues (FIG. 1B) [23]. Several cytoskeletal proteins involved in organization of the muscle sarcomere have recently been shown to contain such structural units. By sequence comparison, the highest homology is detected between myotilin and the region of human striated muscle titin, which contains the Z-disk associated Ig-domains 7 and 8 (FIG. 1C) (residues 1406–1621 of titin)[4]. The sequences within the compared regions are 31% identical and 53% conserved without any introduced gaps. A similarity comparison using the Clustal method indicates a 38.3% similarity between this region of myotilin and titin. The sequence similarity between myotilin and titin is restricted to the Ig-domains of myotilin. Other characteristic structural features of titin, the fn(III)-type domains, the specific sequences of Z-disk, I-band and M-band, or the repeating KSP phosphorylation motif [4] are not present in myotilin. However, the sequence prediction of myotilin reveals several other possible sites for phosphorylation, three of them in the serine-rich region.

Organization of Myotilin Gene

Figure 2:
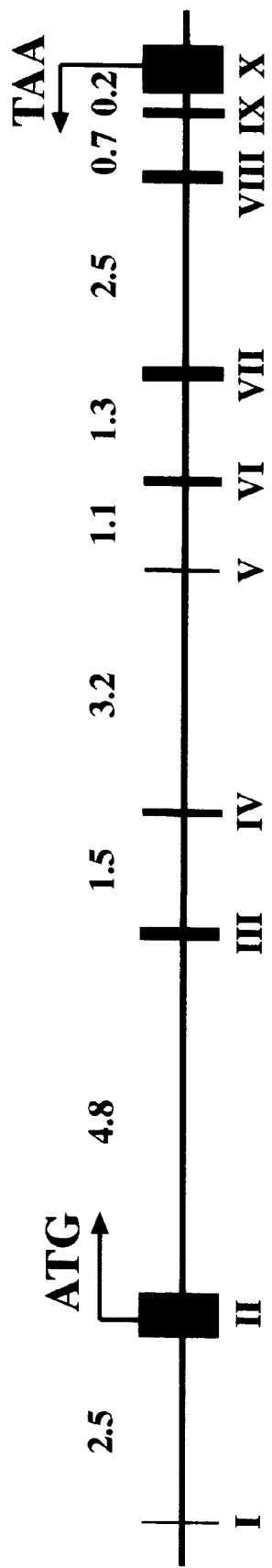
FIG. 2. Organization of the myotilin gene. Exons (vertical black boxes) numbered with Roman numerals and introns are shown in scale. The position of translation initiation signal in exon II and the translation stop codon in exon X is indicated. The sizes of introns are in kb.

The organization of myotilin gene was determined by comparing the myotilin cDNA with the genomic sequence from chromosome 5 Pac clone 9c13 (Genbank accession number AC006084). All splice junction sequences are in agreement with the GT-AG consensus (Table 1). The exon/intron boundaries were further confirmed by amplification of each exon from a commercial P1 clone with intron specific primers (not shown). The gene is composed of ten exons, and the translation initiation signal is in exon II (FIG. 2). Thus the small 69 bp first exon is not translated. The size of the entire gene is under 20 000 bp without the promoter region. The sequences coding for the Ig-domains are located in exons VI and VII (first Ig-domain) and in exons VIII and IX (second Ig-domain).

TABLE 1

Exon-intron structure and splice junction sites of the human myotilin gene.

| Exon No. | Size (bp) | 5' splice donor | | Intron size (kb) | 5' splice acceptor | |
|---|---|---|---|---|---|---|
| I | 69 | GGAACTACGGgtaagtccct | (SEQ ID NO:4) | 2.5 | cctttgaagGAACAATATT | (SEQ ID NO:5) |
| II | 567 | TGGATTCCAAgtaagtgaat | (SEQ ID NO:6) | 4.8 | cttttaaagCTATCAACAG | (SEQ ID NO:7) |
| III | 175 | TGGAAATCAAgtgggcaaga | (SEQ ID NO:8) | 1.5 | ttctctaaagCGTCTAACAT | (SEQ ID NO:9) |
| IV | 102 | AGACTCGCAGgtaagttaaa | (SEQ ID NO:10) | 3.2 | taatttcaagCAACACAACT | (SEQ ID NO:11) |
| V | 50 | CACAAGTAAGgtaaaaaatt | (SEQ ID NO:12) | 1.1 | attcttgtagAAGTAGATCA | (SEQ ID NO:13) |
| VI | 133 | GGACTTCAAAgtaagagaag | (SEQ ID NO:14) | 1.3 | ttctttctagGTGAGTGGAC | (SEQ ID NO:15) |
| VII | 208 | GATGTCCTTGgtaagcctcc | (SEQ ID NO:16) | 2.5 | taatatatagCAAAAGAACA | (SEQ ID NO:17) |
| VIII | 166 | ACCGAATAAGgtaggatatg | (SEQ ID NO:18) | 0.7 | tttatttcagCTTATATCAA | (SEQ ID NO:19) |
| IX | 134 | GACGTTACGGgtatgtcata | (SEQ ID NO:20) | 0.2 | tctatttcagCACGTCCAAA | (SEQ ID NO:21) |
| X | 641 | | | | | |

Chromosomal Localization of Myotilin

Figure 3:
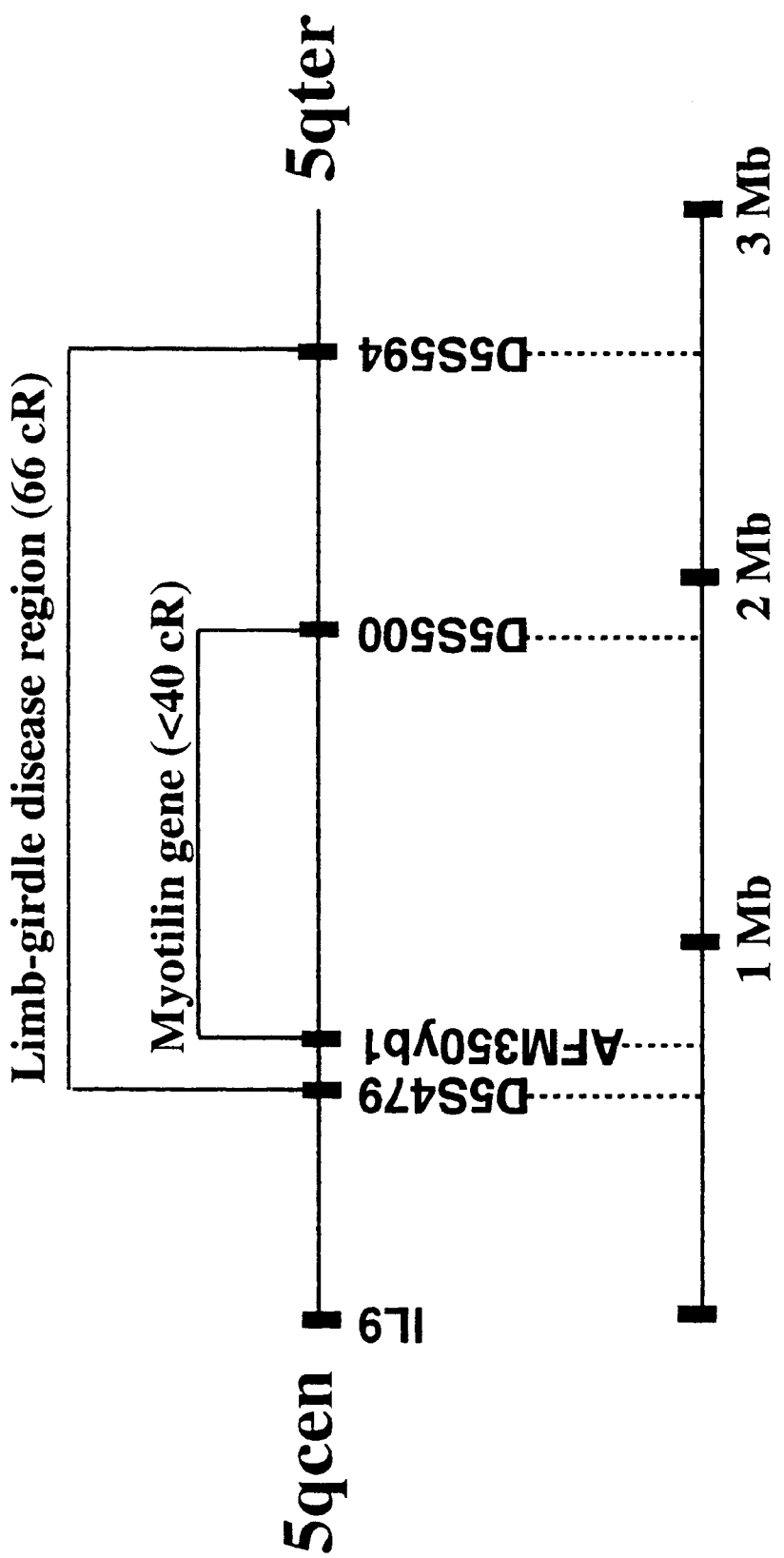
FIG. 3. Integrated map of chromosome 5 in the myotilin gene region. Distances between markers are based on combined genetic and physical mapping information. The myotilin gene is located in chromosome 5q31, 141 cM from top of chromosome 5 linkage group [24] and maps within the 2 Mb limb-girdle muscular dystrophy (LGMD1A) critical region [16] thus being a positional candidate gene for the disease. IL9, the interleukin-9 gene. The orientation of the chromosome is indicated (centromere to the left).

The chromosomal localization of myotilin gene was determined by radiation hybrid mapping. The myotilin gene was mapped to chromosome 5q31 between the markers AFM350yb1 and D5S500 (FIG. 3). The gene causing an autosomal, dominantly inherited limb-girdle muscular dystrophy (LGMD) 1A has been mapped to chromosome 5q31 between the markers D5S479 and D5S594 [16]. The myotilin gene is inside this reported area. Taken all the data together, myotilin is a candidate gene for LGMD1A.

Expression Pattern of Myotilin

Figure 4:
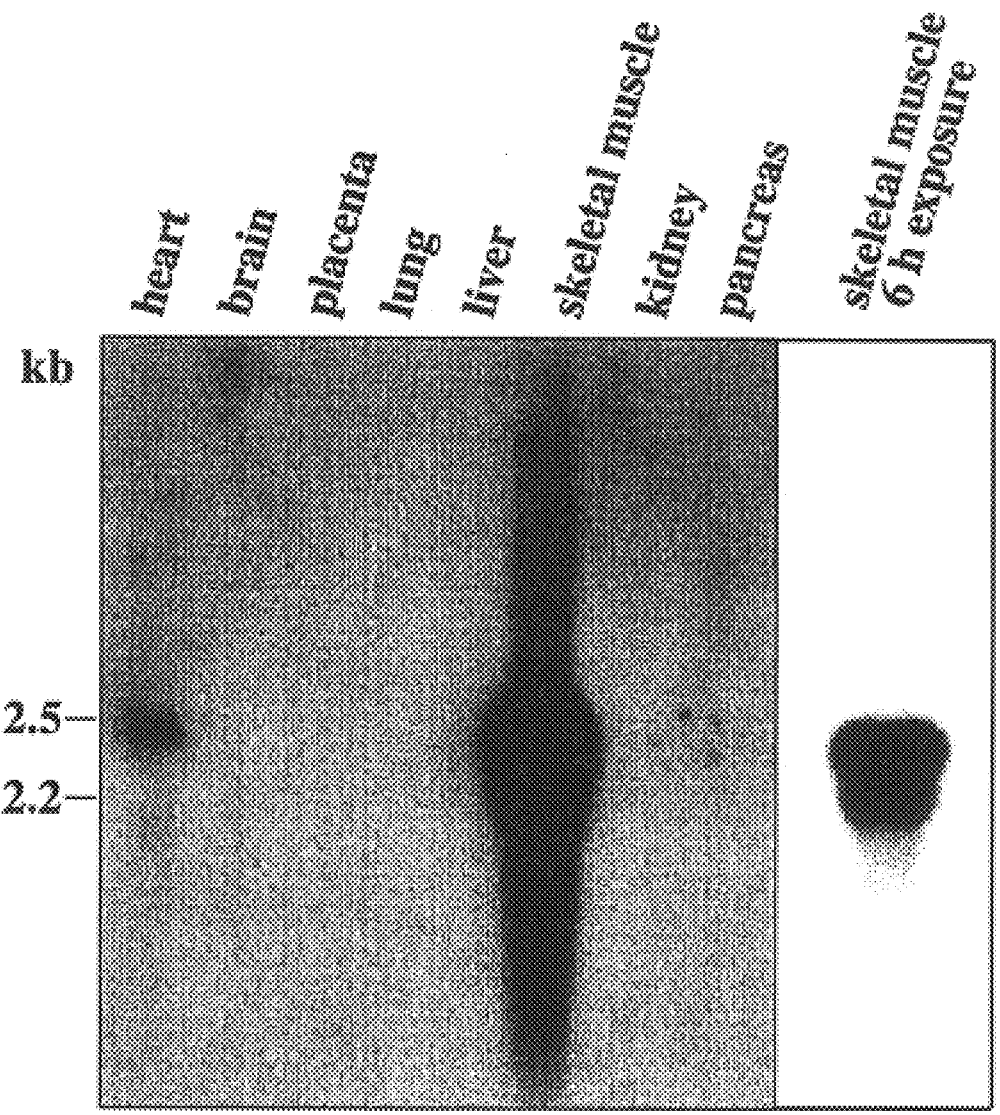
FIG. 4. Northern blot analysis of myotilin. A commercial multiple tissue mRNA filter was probed with a $^{32}$P-labeled 320 bp fragment of myotilin cDNA. The filter was exposed for 20 h. The probe hybridizes strongly with skeletal muscle RNA and weakly with cardiac muscle RNA, whereas other indicated tissues are negative. The right lane shows a 6h exposure of the skeletal muscle mRNA, in order to demonstrate two different transcript sizes (2.2 and 2.5 kb).
Figure 5:
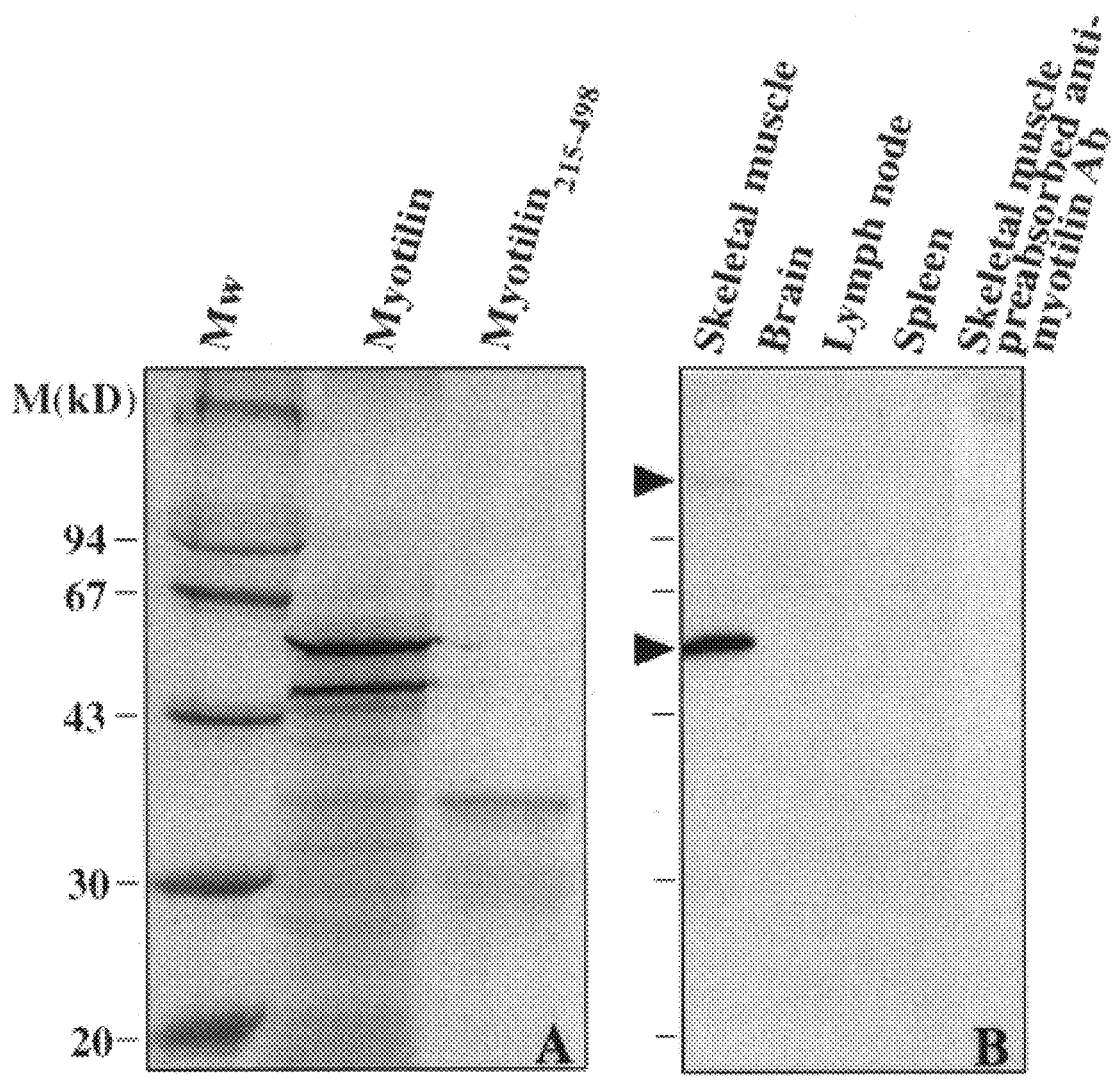
FIG. 5A. In vitro translation of myotilin. The myotilin cDNA was in vitro translated using a coupled reticulocyte lysate kit. A 57 kDa protein band representing the full-size protein is detected. The smaller 45 kDa band in the translation of full length cDNA is apparently due to aberrant translational starting point in the sequence. Myotilin$_{215-498}$ is a deletion construct used in two-hybrid experiments. Mw=molecular weight markers.
FIG. 5B. Western blot analysis of myotilin. Lysates from the indicated tissues were used for immunoblotting with affinity purified myotilin antibody. Western blotting of human skeletal muscle reveals a strong 57 kDa band and a fainter 110 kDa band (arrowheads), whereas the non-muscular tissues show no reactivity. Preabsorption of the myotilin antibody with 5-fold molar excess of the antigenic peptide results in loss of immunoreactivity from skeletal muscle lysate (right lane).

By Northern blot analysis we detected two different transcripts (2.2 and 2.5 kb) strongly expressed in skeletal muscle and weakly in the heart (FIG. 4). The two transcripts in the heart are only seen after a prolonged exposure (not shown). Smooth muscle and several non-muscular tissues, including brain, placenta, lung, liver, kidney and pancreas, did not contain detectable mRNA. In vitro translation of the full-length cDNA yielded a 57 kDa polypeptide, which is in agreement with the mass of myotilin estimated from the cDNA sequence (FIG. 5A).

We raised an antibody against myotilin by immunizing rabbits with a synthetic branched 17 amino acid peptide encompassing residues 352–368 (see FIG. 1A). In Western blotting this antibody revealed a 57 kDa protein band and a fainter band near 110 kDa from skeletal muscle but not from smooth muscle or non-muscular tissues (FIG. 5B). The reactivity could be blocked by incubating the antibody with 5-fold molar excess of the corresponding peptide (FIG. 5B). Both the mRNA and immunoblotting data thus indicate that myotilin is a muscular protein with a clearly restricted expression pattern. The identity of the 110 kDa band is unclear. As it migrates at a region twice the size of a myotilin monomer and as myotilin is able to form intermolecular interactions (see below), the band possibly represents a myotilin dimer. Upon treatment of tissues with 1% Triton X-100 or with 1M KCl, myotilin was retained in the insoluble fraction suggesting a cytoskeletal association (data not shown).

Subcellular Localization of Myotilin in Skeletal Muscle

Figure 6:
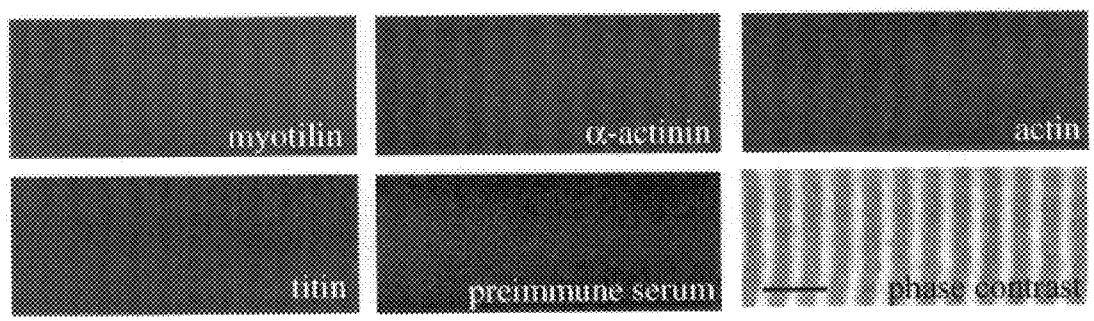
FIG. 6. Immunolocalization of myotilin in purified myofibrils. Bundles of bovine myofibrils were isolated as described in Materials and methods and stained with antibodies against myotilin, α-actinin, actin, titin and a rabbit preimmune IgG. All analyzed proteins localize to I-bands in sarcomeres but the staining patterns differ. Myotilin and α-actinin decorate the middle of I-bands, whereas actin staining is more diffuse. Titin is detected as a doublet staining the junctions of A- and I-bands. The phase contrast image demonstrates the sarcomeric structure, where the light bands are thin filaments (I-bands) and the dark ones are thick filaments (A-bands). Bar=5 μm.

To characterize the subcellular localization of myotilin we isolated bundles of striated muscle myofibrils and stained them using the affinity purified peptide antiserum. The immunostaining pattern was compared to several characterized components of the sarcomere (FIG. 6). Myotilin staining was detected in the I-bands. The staining pattern was reminiscent of α-actinin, which is known to decorate the Z-lines of the I-bands. Actin, the major component of thin filaments, gave a more diffuse staining pattern along the entire I-bands. A titin mAb, which recognizes an epitope at junctions of thin and thick filaments revealed a staining pattern of a doublet band at each sarcomere. The immunolocalization data demonstrates that myotilin is an integral component of striated muscle sarcomeres.

Figure 7A:
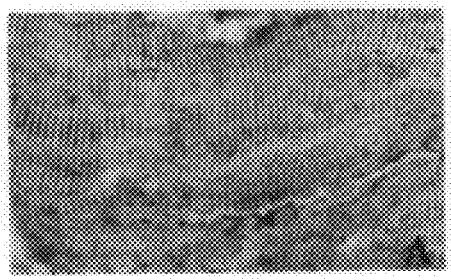
FIGS. 7A to 7D. Immunohistochemical staining of myotilin in frozen sections of human skeletal muscle. Frozen sections of skeletal muscle were analyzed by immunoperoxidase technique using an affinity purified myotilin antibody (A–C) or a control antiserum (D). Myotilin staining is detected in the I-bands of sarcomeres (A), and in transverse sections, also along the sarcolemma of muscle fibers (B). Positive reactivity is also detected in muscular nerves (C). (D) shows a control staining with preimmune serum.
Figure 7B:
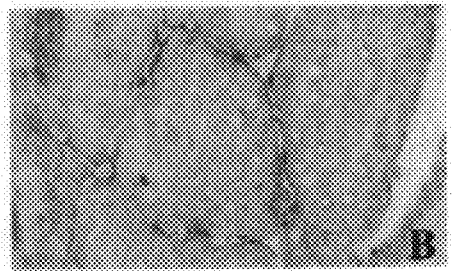
Figure 7C:
Figure 7D:
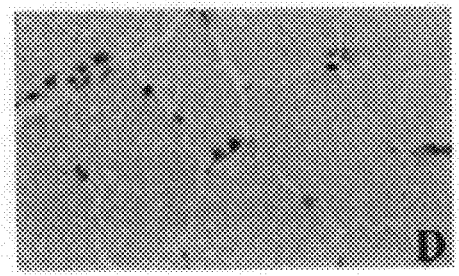

To further study the localization of myotilin in the striated muscle we performed immunohistochemical analyses of frozen tissue sections with the myotilin antibody. In perpendicular sections, where the organization of sarcomeres was visible, we could detect a periodical cross-striated staining of myotilin (FIG. 7A), which was consistent with the pattern in isolated myofibrils. Especially in transverse sections (FIG. 7B) the myotilin staining was also localized at the plasma membrane indicating that myotilin is also present at the sarcolemma. In addition to these findings, myotilin antibody stained intramuscular nerve fibers (FIG. 7C). The preimmune serum gave no reactivity (FIG. 7D).

Myotilin Forms Intermolecular Interactions and Directly Binds α-actinin in vitro We used the yeast two-hybrid method to study protein interactions of myotilin. Among the tested partners, the strongest interactions were seen between myotilin and α-actinin (a construct containing spectrin-like repeats R1–R4) and between myotilin molecules (FIGS. 8A–C). α-actinin is known to form dimers via spectrin-like repeats [25, 26] and this could be verified also in our two-hybrid analysis (FIG. 8B). However, quantitation of the β-galactosidase values indicate that the intensity of the reaction was weaker than the interaction between α-actinin and myotilin and between two myotilin molecules (FIG. 8C). An $NH_2$-terminal deletion construct containing the Ig-domains, myotilin$_{215-498}$ bound full-length myotilin, but did not bind α-actinin (R1–R4). We were unable to express myotilin$_{215-498}$ as a bait to test whether the intermolecular interaction of myotilin is mediated by the COOH-terminal Ig-domain containing region or by $NH_2$-terminal association to the COOH-terminal part. The interaction between myotilin and α-actinin was further tested by an affinity precipitation assay, using in vitro translated $^{35}$S-labelled myotilin and GST-α-actinin constructs bound to glutathione-Agarose. Myotilin bound the COOH-terminal half of α-actinin (R3/R4/EF-hand), but not the $NH_2$-terminal half (ABD/R1/R2) or GST alone (FIGS. 8D–E). Based on the two-hybrid and affinity precipitation results, residues important for α-actinin binding reside in the first 215 $NH_2$-terminal residues of myotilin and the myotilin binding site in α-actinin apparently locates within spectrin-like repeats 3 and 4.

Effect of Transfected Myotilin on Actin-Cytoskeleton and Cell Growth

Figure 9:
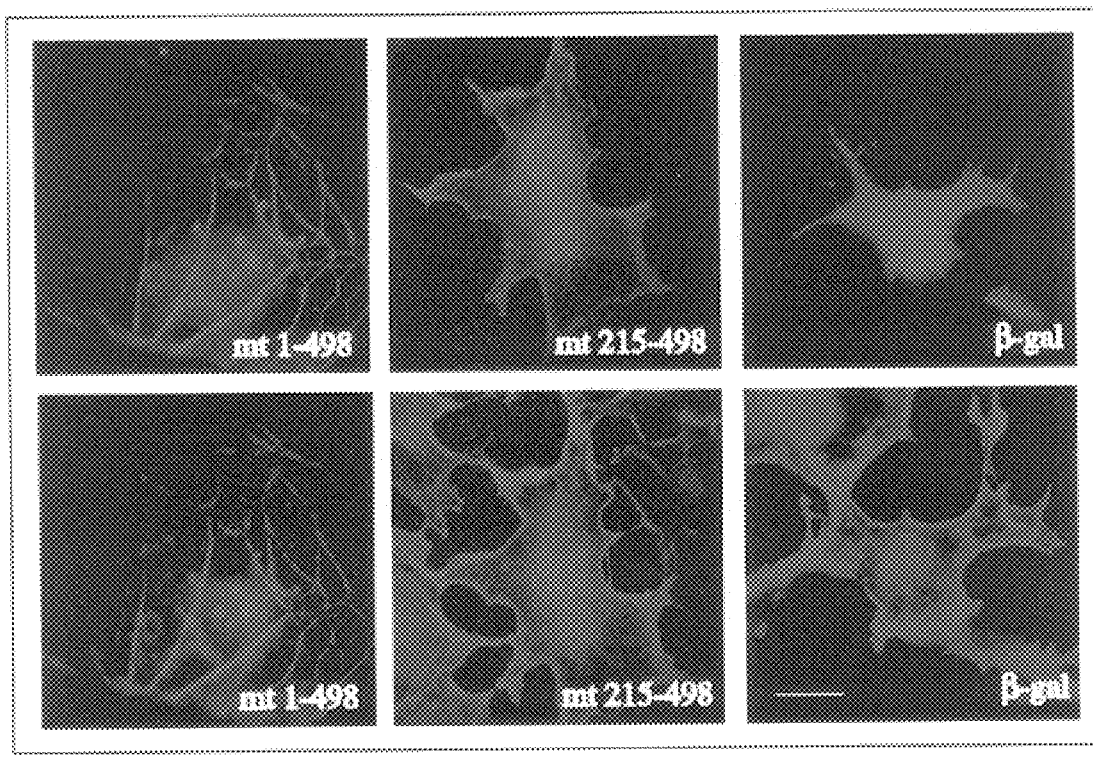
FIGS. 9A to 9F. Effect of myotilin in the organization of actin-containing cytoskeleton in COS cells. On the left, COS cells transiently transfected with myotilin cDNA (mt 1–498); in the middle cells transfected with a COOH-terminal construct, myotilin$_{215-498}$ (mt 215–498); on the right, a transfection control β-galactosidase cDNA (β-gal). (A–B) show staining of myotilin, (C) shows β-galactosidase staining. (D–F) are double staining of the same cells for F-actin. Note thick F-actin and myotilin containing bundles in (A) and (D). Myotilin$_{215-498}$ colocalizes with F-actin, but organization of actin does not differ from control cells. β-galactosidase control does not show any specific localization. Bar=20 μm.

The cellular localization and function of myotilin was further analyzed by transiently transfecting HA-epitope tagged full length myotilin and a COOH-terminal myotilin construct (myotilin$_{215-498}$) into COS-1 cells that do not express endogenous protein. The myotilin$_{215-498}$ construct was confirmed by in vitro translation to yield a proper size polypeptide (FIG. 5A). β-galactosidase DNA was used as a transfection control. After 72 hours the cells were fixed and double stained for myotilin or β-galactosidase and actin. Myotilin$_{215-498}$ showed partly a diffuse cytoplasmic staining pattern but also submembraneous accumulation which colocalized with cortical actin visualized by phalloidin staining (FIGS. 9B,E). In contrast, full length myotilin localized within the filament network of the cell body and phalloidin staining revealed a strict colocalization with F-actin in these filaments. Remarkably, we could notice formation of thick F-actin containing bundles in COS-1 cells (FIGS. 9A,D), whose actin-containing skeleton is poorly organized under these culture conditions. β-galactosidase showed a diffuse cytoplasmic distribution and did not colocalize with F-actin (FIGS. 9C,F).

Figure 10:
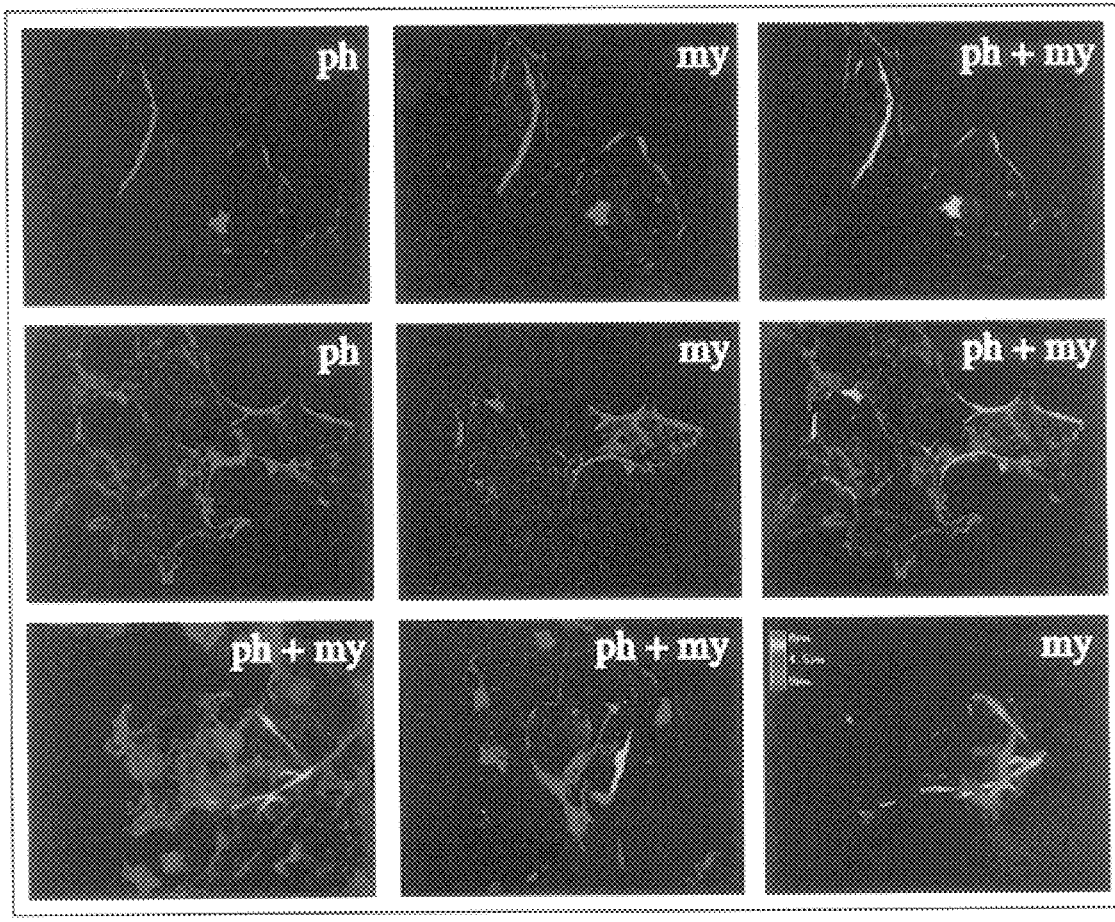
FIG. 10. Confocal analysis of COS cells expressing myotilin. COS cells transfected with myotilin cDNA were fixed, double-stained for F-actin (ph) and myotilin (my) and analyzed by a confocal microscope. Images on the top right and middle right are composites of corresponding phalloidin (red) and myotilin (green) staining. Areas of overlapping distribution are in yellow. Note the thick cytoplasmic F-actin and myotilin-containing structures in top panel and the submembraneous cortical structures in the middle panel. On the bottom are shown composite images of phalloidin-(red) and myotilin-staining (green) of one transfected cell shown at 2 μm (left) and 6 μm (middle) above the growth substratum demonstrate a haphazard arrangement of the F-actin and myotilin-containing structures. On the bottom right, an overlay of myotilin-staining of sections at 1 μm interval through the entire cell is shown. The color coding indicates distance (μm) from the substratum. Note lack of staining at the ventral surface of the cell. Bar=10 μm.

The myotilin-induced actin-containing structures were further characterized by confocal microscopy (FIG. 10). Typically, the actin bundles were present in the cell body, although in some cells they were located subcortically in the cell periphery (FIG. 10, middle row). Sectioning of the cells revealed that the F-actin and myotilin-containing structures were often haphazardly arranged at different levels in the cytoplasm. This is visualized in the bottom panel of FIG. 10, in which images on the left and in the middle are composites of F-actin and myotilin staining at two different planes of the same cells and the image on the right is an overlay of the myotilin labelling in the entire cell. Importantly, the structures were not present at the ventral surface of the transfected cells indicating that they are not stress fibers. The effect of myotilin on actin-organization is not reminiscent of changes induced by overexpression of previously characterized actin-organizing proteins and suggests a unique mechanism of action.

Effect of Myotilin on Yeast Cell Actin and Cell Growth

Figure 11A:
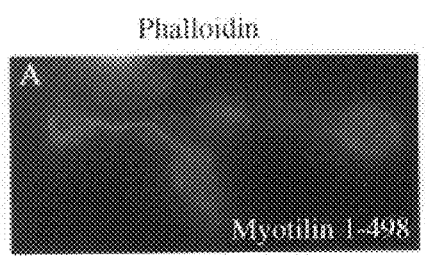
FIGS. 11A to 11F. The effect of myotilin on yeast cell cytoskeleton and growth. Yeast cells expressing myotilin (A and B) and control cells (C and D) were stained with rhodamine-phalloidin to decorate F-actin (A and C) or with calcofluor to stain cell wall carbohydrates (B and D). Note that the myotilin expressing cells are elongated, grow in rows and are connected with thick actin-bundles suggesting a defective cell separation event. E. Growth rate of cells expressing various myotilin fragments. The numbers indicate amino acids of myotilin included in the constructs. Full-length myotilin and myotilin$_{215-498}$ reduce cell growth. JG4-5=an empty vector. F. Growth rate of cells expressing myotilin and/or control proteins in two different expression vectors. The strongest growth inhibitory effect is caused by expression of myotilin or its COOH-terminal fragment in both vectors. The growth rate of cells expressing ezrin, a control actin-organizing protein, does not differ from growth of cells transfected with empty vectors. α-actinin=spectrin-like repeats of chicken gizzard α-actinin, EG202 and JG4-5=empty vectors.
Figure 11B:
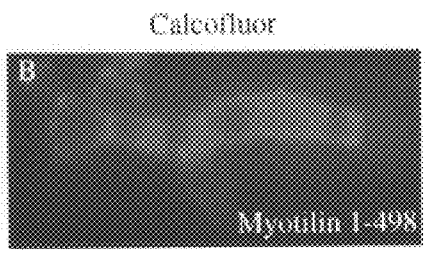
Figure 11C:
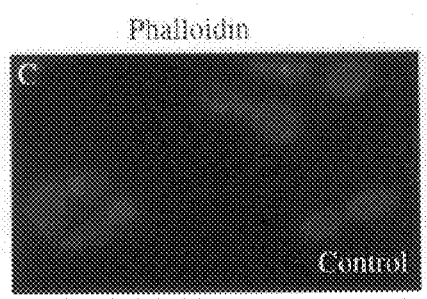
Figure 11D:
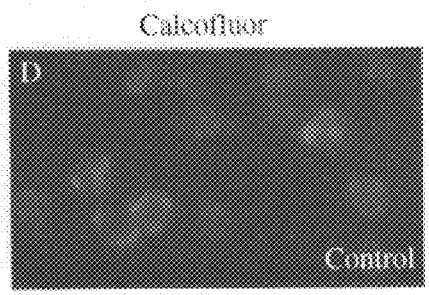
Figure 11E:
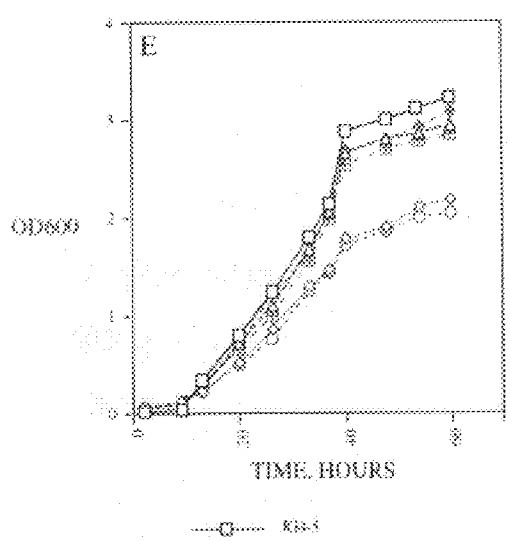
Figure 11F:
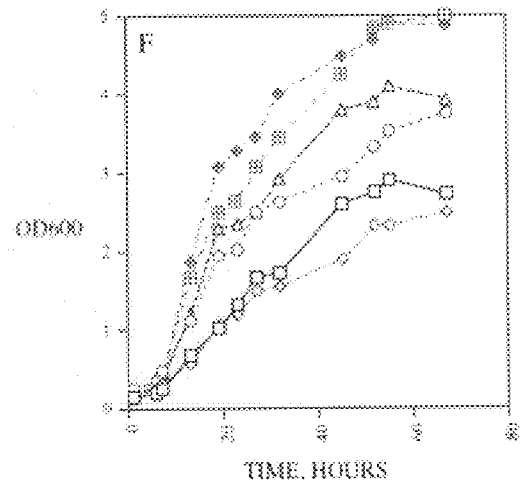

The biological functions of myotilin were also studied by expressing myotilin in *Saccharomyces cerevisiae*. Induction of myotilin expression resulted in reorganization of actin into thick filaments not detected in control cells (FIG. 11A and C). The myotilin expressing cells grew in rows and the filaments continued from one cell to another (FIG. 11A). This result indicates that the actin organizing property of myotilin is conserved within different organisms. Expression of myotilin or its COOH-terminal part resulted in inhibition of cell growth, whereas expression of $NH_2$-terminal constructs (1–150 and 1–250) or a shorter COOH-terminal construct (270–472) did not have a similar effect (FIG. 11E). This growth-inhibitory function parallelled with morphogenic changes in yeast cells. When myotilin was expressed simultaneously in two different expression vectors, the growth inhibiting effect was stronger than the effect produced by a single vector indicating that the effect is dependent on the level of protein expression (FIG. 11F). In this experiment, expression of an irrelevant cytoskeletal actin-binding protein, ezrin, did not affect cell growth, further demonstrating the specificity of the effect of myotilin.

Experimental

| Abbreviations | |
| --- | --- |
| ABD | actin-binding domain |
| CH | calponin homology |
| EST | expressed sequence tag |
| F-actin | filamentous actin |
| fn | fibronectin |
| Ig | Immunoglobulin |
| LGMD | Limb Girdle Muscular Dystrophy |
| MBP | Myosin Binding Protein |
| MLCK | Myosin Light Chain Kinase |
| R | repeat |

Materials and Methods cDNA Cloning of Myotilin and Sequence Analysis

A partial cDNA was used for screening of the full-length myotilin cDNA from a skeletal muscle library (Stratagene, La Jolla, Calif.). Positive clones were sequenced with an ABI 310 Genetic Analyzer (Perkin-Elmer, Foster City, Calif.). Protein database searches were done with BLAST program. Sequence alignments between Ig-domains of myotilin and other cytoskeletal proteins were performed with the MegAlign software (DNASTAR). The domain predictions were obtained from Pfam server. Protein motif predictions were done with Protein Family alignment Pfam 2.1 and with Motif.

Genomic Structure of Myotilin Gene

The organization of myotilin gene was determined by comparing the myotilin cDNA with the genomic sequence from chromosome 5 Pac clone 9c13 (Genbank accession number AC006084). A commercial P1 clone (GenomeSystems Inc., St. Louis, Mich., searched by PCR with myotilin primers) was used for amplification and sequencing of exon-intron boundaries.

Chromosomal Localization of Myotilin

The chromosomal localization of myotilin gene was determined by radiation hybrid mapping using the Genebridge II panel. PCR assays were performed as duplicates and the resulting data vector was analyzed using Whitehead Genome Center server.

Production of Myotilin Antibody

A polyclonal antibody was raised in rabbits using a synthetic branched, lysine-cored 17 amino acid peptide of myotilin (marked in FIG. 1 with a scattered line) as the antigen. After five immunizations, rabbits were bled. The specific antibody was purified in an affinity column using a corresponding single chain peptide coupled to CNBr-activated Sepharose 4B (Pharmacia, Uppsala, Sweden) as the ligand. The specificity of the rabbit antibody was verified by reactivity with appropriate GST-fusion protein constructs in Western blot analysis (data not shown) and by cross-blocking experiments, in which five-fold molar excess of the specific peptide but not an irrelevant myotilin peptide (residues 199–217) absorbed the reactivity.

mRNA and Protein Studies

Northern blot analysis was performed with a multiple tissue mRNA filter (Clontech Laboratories, Inc., Palo Alto, Calif.) using a $^{32}$P-labelled 320 bp myotilin cDNA fragment, which encodes amino acids 369–471, as a probe. In vitro translations were performed with a coupled reticulocyte lysate kit (Promega, Madison, Wis.) using $^{35}$S-labelled methionine for detection. The templates were full-length myotilin and a construct containing amino acids 215–498 (myotilin$_{215-498}$) in Bluescript plasmid vector (Stratagene). For Western blotting, fresh tissues were homogenized in reducing Laemmli buffer. Equal amounts of protein, as estimated by Coomassie blue staining, were separated in 8% SDS-PAGE and transferred to nitrocellulose filters (Schleicher & Schuell GmbH, Dassel, Germany). The filters were probed with the myotilin antibody or with a control preimmune serum, followed by peroxidase conjugated goat anti-rabbit IgG (Dako A/S, Copenhagen, Denmark) and ECL detection (Pierce, Rockford, Ill.).

Localization of Myotilin in Myofibrils

Bundles of bovine and human myofibrils were isolated as described [27], cytocentrifuged onto objective slides, fixed in −20° C. methanol, and reacted with mAb against actin (AC 40, Sigma Chemical Co., St. Louis, Mo.), titin (T11, Sigma), α-actinin (67CB11) [28] and a control mAb X63 (ATCC, Maryland, USA), or with affinity purified anti-myotilin antibody or the corresponding preimmune IgG. Secondary antibodies were FITC-conjugated goat anti-mouse IgG (Cappel Research Products, Durham, N.C.) and TRITC-conjugated goat anti-rabbit F(ab)2 fragment (Jackson ImmunoResearch Laboratories, Inc., West Grove, Pa.). Staining of bovine and human myofibrils yielded identical results.

Immunohistochemistry

Frozen 2 μm sections of human skeletal muscle were immobilized on poly-L-lysine-coated glass slides, fixed with cold acetone and immediately air-dried. For immunohistochemical staining the sections were reacted with 1:100 dilution of affinity-purified myotilin Ab or rabbit preimmune IgG at similar concentration. The antibody was detected with Elite Vectastain ABC kit (Vector Laboratories, Inc., Burlingame, Calif.) according to manufacturer's instructions. The slides were briefly counterstained with hematoxylin-eosin.

Yeast Two-hybrid Analysis and in vitro Binding Assay

Full length myotilin, myotilin$_{215-498}$ and spectrin-like repeats R1–R4 (residues 267–749) of chicken smooth muscle α-actinin (kindly provided by Dr. D. Critchley, University of Leicester, UK) were subcloned into EG202 and JG4-5 plasmids for two-hybrid analysis [29]. The COOH-terminal construct of myotilin was subcloned from a partial cDNA sequence obtained from the skeletal muscle library screen. The authentity of the constructs was verified by sequencing. The genotype of the S. cerevisiae strain BOY1, kindly provided by P. Ljungdahl, Ludwig Institute for Cancer Research, Stockholm, Sweden, is MATαhis3 trp1 leu2::6LexAop-LEU2 URA3::8LexAop-Gal1-LacZ. Boy1 mating type a was made using the YCPHO CUT4 plasmid [30]. Yeast strains were grown at 30° C. in rich medium or in synthetic minimal medium with appropriate amino acid supplements. Bait and prey constructs were transformed into BOY1-yeast of both a and a mating type using the TRAFO protocol and plated on selection plates. Clones were grown to late logarithmic phase in selective medium. For analysis of fusion protein expression, yeast cells from 1 ml of overnight culture were lysed in reducing Laemmli sample buffer, the samples were boiled and analyzed by SDS-PAGE and immunoblotting. Baits and preys were grown on selection plates, replica plated together on rich media plates for mating overnight and replica plated on double (tryptophane and histidine) or triple (tryptophane, histidine and leucine) selection with or without 5-bromo-4-chloro-3-indolyl-β-D-galactopyranoside (X-gal)(Boehringer) for selection of interactions.

For the in vitro binding assay, GST-α-actinin fusion proteins, ABD/R1/R2, R3/R4/EF [25] or GST alone were produced in E. coli and purified with glutathione-Agarose beads (Pharmacia). 2 μg of fusion proteins on glutathione beads were reacted with 20 μl of in vitro translated,$^{35}$S-labelled myotilin in 10 mM Tris-HCl, pH 7.5, 5 mM EDTA, 130 mM KCl, 0.05% Tween 20. After washes with the same buffer, bound material was eluted by boiling in Laemmli buffer, subjected to SDS-PAGE and detected by autoradiography.

Localization of Myotilin in Transfected COS-1 cells

In transfection studies full length myotilin and myotilin$_{215-498}$ construct in an HA-tagged pAHP plasmid (a derivative of pcDNA3, Invitrogen, San Diego, Calif.) and a control SV-β-galactosidase vector (Clontech) were used. COS-1 cells plated on 6 cm tissue culture dishes were transfected with 5 μg of appropriate plasmid cDNA using Superfect (Qiagen GmbH, Hilden, Germany) and grown on glass coverslips. After 72 hours, cells were fixed in 3.5% paraformaldehyde at +4° C. for 10 min. and permeabilized in 0.1% Triton X-100. Transfected protein was immunoreacted with anti-HA mAb (12CA5, Boehringer GmbH, Mannheim, Germany) or anti-β-galactosidase mAb (Boehringer) followed by FITC-conjugated goat anti-mouse IgG. F-actin was simultaneously visualized with rhodamine-labelled phalloidin (Molecular Probes, Eugene, Oreg.). The specimens were viewed with a Zeiss Axiophot II epifluorescence microscope (Carl Zeiss, Oberkochen, Germany) or alternatively, with a confocal 410 Invert Laser Scan microscope (Carl Zeiss).

Effect of Myotilin on Yeast Actin and Cell Growth

The effect of myotilin on yeast actin cytoskeleton and growth rate was studied as follows. For actin staining, cells expressing myotilin or cells transfected with an empty vector were fixed in 4% paraformaldehyde. F-actin was visualized with rhodamine-labelled phalloidin (Molecular Probes, Eugene, Oreg.) and the cell wall with calcofluor (1 mg/ml) (Sigma). After washings the cells were resuspended in DABCO mounting solution. For analysis of the effect of myotilin in cell growth, haploid cells transfected with myotilin in JG4-5 vector were grown in glucose, washed and an equal amount of cells with different myotilin constructs were added into galactose-containing growth medium for induction of protein expression. Diploid cells expressing two different proteins from the JG4-5 and EG202 vectors were grown in galactose from the initiation of the experiment. At indicated time points a small aliquot of cells was sonicated and OD$_{600}$ was measured using a spectrophotometer.

References

1. Fürst, D.O. and Gautel, M. (1995) The anatomy of a molecular giant: How the sarcomere cytoskeleton is assembled from immunoglobulin superfamily molecules. *J. Mol. Cardiol.* 27:951–959.
2. Keller, T.C. 3rd. (1995) Structure and function of titin and nebulin. *Curr. Opin. Cell Biol.* 7:32–38.
3. Blanchard, A., Ohanian, V. and Critchley, D. (1989) The structure and function of α-actinin. *J. Muscle Res. Cell Motil.* 10:280–289.
4. Labeit, S. and Kolmerer, B. (1995) Titins: giant proteins in charge of muscle ultrastructure and elasticity. *Science* 270:293–296.
5. Fowler, V.M. (1996) Regulation of actin filament length in erythrocytes and striated muscle. *Curr. Opin. Cell Biol.* 8:86–96.
6. Gautel, M., Goulding, D., Bullard, B., Weber, K. and Fürst, O. (1996) The central Z-disk region of titin is assembled from a novel repeat in variable copy numbers. *J. Cell Sci.* 109:2747–2754.
7. Maruyama, K. (1997) Connectin/titin, giant elastic protein of muscle. *Faseb J.* 11:341–345.
8. Young, P., Ferguson, C., Banuelos, S. and Gautel, M. (1998) Molecular structure of the sarcomeric Z-disk: two types of titin interaction lead to an asymmetrical sorting of α-actinin. *EMBO J.* 17:1614–1624.
9. Brown, R.H. Jr. (1996) Dystrophin-associated proteins and the muscular dystrophies: A glossary. *Brain Pathol.* 6: 19–24.
10. Ozawa, E., Noguchi, S., Mizuno, Y., Hagiwara, Y. and Yoshida, M. (1998) From dystrophinopathy to sarcoglycanopathy: evolution of a concept of muscular dystrophy. *Muscle Nerve* 21: 421–438.
11. Olson, T.M., Michels, V.V., Thibodeau, S.N., Tai, Y-S. and Keating, M.T. (1998) Actin mutations in dilated cardiomyopathy, a heritable form of heart failure. *Science* 280:750–752.
12. Towbin, J.A. (1998) The role of cytoskeletal proteins in cardiomyopathies. *Curr. Opin. Cell Biol.* 10: 131–139.
13. Laing, N.G., Wilton, S.D., Akkari, P.A., Dorosz, S., Boundy, K., Kneebone, C., Blumbergs, P., White, S., Watkins, H., Love, D.R. and Haan, E. (1995) A mutation in the α-tropomyosin gene TPM3 associated with autosomal dominant nemaline myopathy. *Nat. Genet.* 9:75–79.
14. Pelin, K., Ridanpää, M., Donner, K.. Wilton. S.. Krishnarajah, J., Laing, N.G., Kolmerer, B., Labeit, S., de la Chapelle, A. and Wallgren-Petterson, C. (1997) Refined localization of the genes for nebulin and titin on chromosome 2q allows the assignment of nebulin as a candidate gene for autosomal recessive nemaline myopathy. *Eur. J. Hum. Genet.* 65:620–626.

15. Haravuori, H., Makela-Bengs, P., Udd, B., Partanen, J., Pulkkinen, L., Somer, H. and Peltonen, L. (1998) Assignment of the tibial muscular dystrophy locus to chromosome 2q31. *Am. J. Hum. Genet.* 62:620–626.
16. Bartoloni, L, Horrigan, S.K., Viles, K.D., Gilchrist, J.M., Stajich, J.M., Vance, J.M., Yamaoka, L.H., Pericak-Vance, M., Westbrook, C.A. and Speer, M.C. (1998) Use of CEPH meiotic breakpoint panel to refine the locus of limb-girdle muscular dystrophy type 1A (LGMD1A) to a 2-Mb interval on 5q31. *Genomics* 54:250–255.
17. Feit, H., Silbergleit, A., Schneider, L.B., Gutierrez, J.A., Fitoussi, R.-P., Reyes, C., Rouleau, G.A., Brais, B., Jackson, C.E., Beckmann, J.S. and Seboun, E. (1998) Vocal cord and pharyngeal weakness with autosomal dominant distal myopathy: clinical description and gene localization to 5q31. *Am. J. Hum. Genet.* 63:1732–1742.
18. Janmey, P.A. and Chaponnier, C. (1995) Medical aspects of the actin cytoskeleton. *Curr. Opin. Cell Biol.* 7:111–117.
19. Assoian, R.K. and Zhu, X. (1997) Cell anchorage and the cytoskeleton as partners in growth factor dependent cell cycle progression. *Curr. Opin. Cell Biol.* 9:86–92.
20. Jordan, M.A. and Wilson, L. (1998). Microtubules and actin filaments: dynamic targets for cancer chemotherapy. *Curr. Opin. Cell Biol.* 10:123–130.
21. Sasse, F., Kunze, B., Gronewold, M. and Reichenbach, H. (1998). The chondramides: Cytostatic agents from myxobacteria acting on the actin cytoskeleton. *J. Natl. Cancer Inst.* 90: 1559–1563.
22. Martin, R.M., Gasser, R.B., Jones, M.K. and Lightowlers, M.W. (1995) Identification and characterization of myophilin, a muscle-specific antigen of *Echinococcus granulosus*. *Molecular & Biochemical Parasitology*. 70:139–48.
23. Williams, A.F. and Barclay, A.N. (1988) The immunoglobulin superfamily-domains for cell surface recozinition. *Annu. Rev. Immunol.* 6:381–405.
24. Laitinen, T., Kauppi, P., Ignatius, J., Ruotsalainen, T., Daly, M.J., Kääriäinen, H., Kruglyak, L., Laitinen, H., de la Chapelle, A., Lander, E.S., Laitinen, L.A. and Kere, J. (1997) Genetic control of serum IgE levels and asthma: linkage and linkage disequilibrium studies in an isolated population. *Hum. Mol. Genet.* 6:2069–2076.
25. Kahana, E. and Gratzer, W.B. (1991) Properties of the spectrin-like structural element of smooth-muscle α-actinin. *Cell Motil. Cytoskel.* 20:242–248.
26. Flood, G., Kahana, E., Gilmore, A.P., Rowe, A.J., Gratzer, W.B. and Critchley, D.R. (1995) Association of structural repeats in the α-actinin rod domain. Alignment of inter-subunit interactions. *J. Mol. Biol.* 252: 227–234.
27. Knight, P.J., and Trinick, J.A. (1982) Preparation of myofibrils. *Methods Enzymol.* 85 Pt B:9–12.
28. Narvanen, O., Narvanen, A., Wasenius, V-M., Partanen, P. and Virtanen, 1. (1987) A monoclonal antibody against a synthetic peptide reveals common structures among spectrins and α-actinin. *FEBS Lett.* 224:156–160.
29. Guyris, J.E., Golemis, E., Chertkov, H. and Brent, R. (1993) Cdi 1, a human G1 and S phase protein phosphatase that associates with Cdk2. *Cell* 75:791–803.
30. Raghuraman, M., Brewer, B. and Fangman, W. (1994) Activation of a yeast replication origin near a double-stranded DNA break. *Genes & Development* 8:554–562.

What is claimed is:

1. An isolated and purified protein that binds α-actinin, said protein comprising the amino acid sequence shown in SEQ ID NO: 2, or an αactinin binding fragment thereof.

2. The isolated and purified protein of claim 1, wherein said α-actinin binding fragment comprises amino acid residues 1–215 of SEQ ID NO: 2.

3. An isolated and purified functional protein fragment comprising amino acid residues 215–498 of SEQ ID NO: 2 that co-localizes with F-actin.

4. An isolated and purified protein comprising the amino acid sequence shown in SEQ ID NO: 2.

5. The isolated and purified protein of claim 4 that co-localizes with F-actin.

6. A composition, comprising the isolated and purified protein of any one of claims 1, 3, or 4, and a pharmaceutically acceptable carrier.

* * * * *

SEQUENCE LISTING

```
<160> NUMBER OF SEQ ID NOS: 21

<210> SEQ ID NO 1
<211> LENGTH: 2244
<212> TYPE: DNA
<213> ORGANISM: Homo sapiens
<220> FEATURE:
<221> NAME/KEY: CDS
<222> LOCATION: (281)..(1774)

<400> SEQUENCE: 1
gggaaggaga tgcctcttcc ttcccttcaa tagtgggtta aacccagctg gcaccctctg      60
gaactacggg aacaatattc ttcaagagaa ggtcactcta ccaaagccag gagcacagta     120
ttctcaggat ctcaacaagg aagagcagac caaggttgct tctgattcct tacaaccttc     180
cgtaattcca ggcttgtggc cccaaattca gggcccacc  cttccaggaa caaatcatta     240
tagtaataat ttgccttcat cttccatata ccaactaagc atg ttt aac tac gaa      295
                                              Met Phe Asn Tyr Glu
                                                1               5 cgt cca aaa cac ttc atc cag tcc caa aac cca tgt ggc tcc aga ttg      343
Arg Pro Lys His Phe Ile Gln Ser Gln Asn Pro Cys Gly Ser Arg Leu
             10                  15                  20 cag cct cct gga cca gaa acc tcc agc ttc tct agc cag acc aaa cag      391
Gln Pro Pro Gly Pro Glu Thr Ser Ser Phe Ser Ser Gln Thr Lys Gln
         25                  30                  35 tct tcc att atc atc cag ccc cgc cag tgt aca gag caa aga ttt tct      439
Ser Ser Ile Ile Ile Gln Pro Arg Gln Cys Thr Glu Gln Arg Phe Ser
     40                  45                  50
```

-continued

| | | |
|---|---|---|
| gcc tcc tca aca ctg agc tct cac atc acc atg tcc tcc tct gct ttc<br>Ala Ser Ser Thr Leu Ser Ser His Ile Thr Met Ser Ser Ser Ala Phe<br>55                            60                       65 | 487 |
| cct gct tct ccc cag cag cat gct ggc tcc aac cca ggc caa agg gtt<br>Pro Ala Ser Pro Gln Gln His Ala Gly Ser Asn Pro Gly Gln Arg Val<br>70                            75                       80                       85 | 535 |
| aca acc acc tat aac cag tcc cca gcc agc ttc ctc agc tcc ata tta<br>Thr Thr Thr Tyr Asn Gln Ser Pro Ala Ser Phe Leu Ser Ser Ile Leu<br>                        90                       95                       100 | 583 |
| cca tca cag cct gat tac aat agc agt aaa atc cct tcc gct atg gat<br>Pro Ser Gln Pro Asp Tyr Asn Ser Ser Lys Ile Pro Ser Ala Met Asp<br>                105                       110                       115 | 631 |
| tcc aac tat caa cag tcc tca gct ggc caa cct ata aat gca aag cca<br>Ser Asn Tyr Gln Gln Ser Ser Ala Gly Gln Pro Ile Asn Ala Lys Pro<br>                120                       125                       130 | 679 |
| tcc caa act gca aat gct aag ccc ata cca aga act cct gat cat gaa<br>Ser Gln Thr Ala Asn Ala Lys Pro Ile Pro Arg Thr Pro Asp His Glu<br>                135                       140                       145 | 727 |
| ata caa gga tca aaa gaa gct ttg att caa gat ttg gaa aga aag ctg<br>Ile Gln Gly Ser Lys Glu Ala Leu Ile Gln Asp Leu Glu Arg Lys Leu<br>150                           155                       160                       165 | 775 |
| aaa tgc aag gac acc ctt ctt cat aat gga aat caa cgt cta aca tat<br>Lys Cys Lys Asp Thr Leu Leu His Asn Gly Asn Gln Arg Leu Thr Tyr<br>                170                       175                       180 | 823 |
| gaa gag aag atg gct cgc aga ttg cta gga cca cag aat gca gct gct<br>Glu Glu Lys Met Ala Arg Arg Leu Leu Gly Pro Gln Asn Ala Ala Ala<br>                185                       190                       195 | 871 |
| gtg ttt caa gct cag gat gac agt ggt gca caa gac tcg cag caa cac<br>Val Phe Gln Ala Gln Asp Asp Ser Gly Ala Gln Asp Ser Gln Gln His<br>200                           205                       210 | 919 |
| aac tca gaa cat gcg cga ctg caa gtt cct aca tca caa gta aga agt<br>Asn Ser Glu His Ala Arg Leu Gln Val Pro Thr Ser Gln Val Arg Ser<br>                215                       220                       225 | 967 |
| aga tca acc tca agg gga gat gtg aat gat cag gat gca atc cag gag<br>Arg Ser Thr Ser Arg Gly Asp Val Asn Asp Gln Asp Ala Ile Gln Glu<br>230                           235                       240                       245 | 1015 |
| aaa ttt tac cca cca cgt ttc att caa gtg cca gag aac atg tcg att<br>Lys Phe Tyr Pro Pro Arg Phe Ile Gln Val Pro Glu Asn Met Ser Ile<br>                250                       255                       260 | 1063 |
| gat gaa gga aga ttc tgc aga atg gac ttc aaa gtg agt gga ctg cca<br>Asp Glu Gly Arg Phe Cys Arg Met Asp Phe Lys Val Ser Gly Leu Pro<br>                265                       270                       275 | 1111 |
| gct cct gat gtg tca tgg tat cta aat gga aga aca gtt caa tca gat<br>Ala Pro Asp Val Ser Trp Tyr Leu Asn Gly Arg Thr Val Gln Ser Asp<br>                280                       285                       290 | 1159 |
| gat ttg cac aaa atg ata gtg tct gag aag ggt ctt cat tca ctc atc<br>Asp Leu His Lys Met Ile Val Ser Glu Lys Gly Leu His Ser Leu Ile<br>                295                       300                       305 | 1207 |
| ttt gaa gta gtc aga gct tca gat gca ggg gct tat gca tgt gtt gcc<br>Phe Glu Val Val Arg Ala Ser Asp Ala Gly Ala Tyr Ala Cys Val Ala<br>310                           315                       320                       325 | 1255 |
| aag aat aga gca gga gaa gcc acc ttc act gtg cag ctg gat gtc ctt<br>Lys Asn Arg Ala Gly Glu Ala Thr Phe Thr Val Gln Leu Asp Val Leu<br>                330                       335                       340 | 1303 |
| gca aaa gaa cat aaa aga gca cca atg ttt atc tac aaa cca cag agc<br>Ala Lys Glu His Lys Arg Ala Pro Met Phe Ile Tyr Lys Pro Gln Ser<br>                345                       350                       355 | 1351 |
| aaa aaa gtt tta gag gga gat tca gtg aaa cta gaa tgc cag atc tcg<br>Lys Lys Val Leu Glu Gly Asp Ser Val Lys Leu Glu Cys Gln Ile Ser<br>360                           365                       370 | 1399 |

```
gct ata cct cca cca aag ctt ttc tgg aaa aga aat aat gaa atg gta    1447
Ala Ile Pro Pro Pro Lys Leu Phe Trp Lys Arg Asn Asn Glu Met Val
        375                 380                 385 caa ttc aac act gac cga ata agc tta tat caa gat aac act gga aga    1495
Gln Phe Asn Thr Asp Arg Ile Ser Leu Tyr Gln Asp Asn Thr Gly Arg
390                 395                 400                 405 gtt act tta ctg ata aaa gat gta aac aag aaa gat gct ggg tgg tat    1543
Val Thr Leu Leu Ile Lys Asp Val Asn Lys Lys Asp Ala Gly Trp Tyr
                410                 415                 420 act gtg tca gca gtt aat gaa gct gga gtg act aca tgt aac aca aga    1591
Thr Val Ser Ala Val Asn Glu Ala Gly Val Thr Thr Cys Asn Thr Arg
            425                 430                 435 tta gac gtt acg gca cgt cca aac caa act ctt cca gct cct aag cag    1639
Leu Asp Val Thr Ala Arg Pro Asn Gln Thr Leu Pro Ala Pro Lys Gln
                440                 445                 450 tta cgg gtt cga cca aca ttc agc aaa tat tta gca ctt aat ggg aaa    1687
Leu Arg Val Arg Pro Thr Phe Ser Lys Tyr Leu Ala Leu Asn Gly Lys
        455                 460                 465 ggt ttg aat gta aaa caa gct ttt aac cca gaa gga gaa ttt cag cgt    1735
Gly Leu Asn Val Lys Gln Ala Phe Asn Pro Glu Gly Glu Phe Gln Arg
470                 475                 480                 485 ttg gca gct caa tct gga ctc tat gaa agt gaa gaa ctt taataactttt    1784
Leu Ala Ala Gln Ser Gly Leu Tyr Glu Ser Glu Glu Leu
                490                 495 accaacattg gaaacagcc aactacacca ttagtaatat atttgattac attttttga    1844
aattaatcca tagctgtatt aacagattat ggttttaatt aggtaatata gttaatatat    1904
atttataata ttatttatcc tttgactctt gcacattcta tgtacccctc cgatttgtga    1964
agcctacagg aaatctgggt atatggattt gtaactgcag aagactatct taaaatacag    2024
gattttaaca tttaagtcat gcacatttaa caattacagg ttataaatta gtatcaactt    2084
tttaaacaca tctaatgctt gtaataacgt ttactggtac tgctttctaa atactgtttt    2144
acccgttttc tcttgtagga atactaacat ggtatagatt atctgagtgt tccacagttg    2204
tatgtcaaaa gaaaataaaa ttcaaatatt taaaacggac                          2244
```

<210> SEQ ID NO 2
<211> LENGTH: 498
<212> TYPE: PRT
<213> ORGANISM: Homo sapiens

<400> SEQUENCE: 2

```
Met Phe Asn Tyr Glu Arg Pro Lys His Phe Ile Gln Ser Gln Asn Pro
1               5                   10                  15

Cys Gly Ser Arg Leu Gln Pro Pro Gly Pro Glu Thr Ser Ser Phe Ser
            20                  25                  30

Ser Gln Thr Lys Gln Ser Ser Ile Ile Gln Pro Arg Gln Cys Thr
        35                  40                  45

Glu Gln Arg Phe Ser Ala Ser Thr Leu Ser Ser His Ile Thr Met
    50                  55                  60

Ser Ser Ser Ala Phe Pro Ala Ser Pro Gln Gln His Ala Gly Ser Asn
65                  70                  75                  80

Pro Gly Gln Arg Val Thr Thr Thr Tyr Asn Ser Pro Ala Ser Phe
            85                  90                  95

Leu Ser Ser Ile Leu Pro Ser Gln Pro Asp Tyr Asn Ser Ser Lys Ile
                100                 105                 110

Pro Ser Ala Met Asp Ser Asn Tyr Gln Gln Ser Ser Ala Gly Gln Pro
```

```
            115                 120                 125
Ile Asn Ala Lys Pro Ser Gln Thr Ala Asn Ala Lys Pro Ile Pro Arg
    130                 135                 140

Thr Pro Asp His Glu Ile Gln Gly Ser Lys Glu Ala Leu Ile Gln Asp
145                 150                 155                 160

Leu Glu Arg Lys Leu Lys Cys Lys Asp Thr Leu Leu His Asn Gly Asn
                165                 170                 175

Gln Arg Leu Thr Tyr Glu Glu Lys Met Ala Arg Leu Leu Gly Pro
            180                 185                 190

Gln Asn Ala Ala Val Phe Gln Ala Gln Asp Asp Ser Gly Ala Gln
        195                 200                 205

Asp Ser Gln Gln His Asn Ser Glu His Ala Arg Leu Gln Val Pro Thr
    210                 215                 220

Ser Gln Val Arg Ser Arg Ser Thr Ser Arg Gly Asp Val Asn Asp Gln
225                 230                 235                 240

Asp Ala Ile Gln Glu Lys Phe Tyr Pro Pro Arg Phe Ile Gln Val Pro
                245                 250                 255

Glu Asn Met Ser Ile Asp Glu Gly Arg Phe Cys Arg Met Asp Phe Lys
            260                 265                 270

Val Ser Gly Leu Pro Ala Pro Asp Val Ser Trp Tyr Leu Asn Gly Arg
        275                 280                 285

Thr Val Gln Ser Asp Asp Leu His Lys Met Ile Val Ser Glu Lys Gly
    290                 295                 300

Leu His Ser Leu Ile Phe Glu Val Val Arg Ala Ser Asp Ala Gly Ala
305                 310                 315                 320

Tyr Ala Cys Val Ala Lys Asn Arg Ala Gly Glu Ala Thr Phe Thr Val
                325                 330                 335

Gln Leu Asp Val Leu Ala Lys Glu His Lys Arg Ala Pro Met Phe Ile
            340                 345                 350

Tyr Lys Pro Gln Ser Lys Lys Val Leu Glu Gly Asp Ser Val Lys Leu
        355                 360                 365

Glu Cys Gln Ile Ser Ala Ile Pro Pro Pro Lys Leu Phe Trp Lys Arg
    370                 375                 380

Asn Asn Glu Met Val Gln Phe Asn Thr Asp Arg Ile Ser Leu Tyr Gln
385                 390                 395                 400

Asp Asn Thr Gly Arg Val Thr Leu Leu Ile Lys Asp Val Asn Lys Lys
                405                 410                 415

Asp Ala Gly Trp Tyr Thr Val Ser Ala Val Asn Glu Ala Gly Val Thr
            420                 425                 430

Thr Cys Asn Thr Arg Leu Asp Val Thr Ala Arg Pro Asn Gln Thr Leu
        435                 440                 445

Pro Ala Pro Lys Gln Leu Arg Val Arg Pro Thr Phe Ser Lys Tyr Leu
450                 455                 460

Ala Leu Asn Gly Lys Gly Leu Asn Val Lys Gln Ala Phe Asn Pro Glu
465                 470                 475                 480

Gly Glu Phe Gln Arg Leu Ala Ala Gln Ser Gly Leu Tyr Glu Ser Glu
                485                 490                 495

Glu Leu

<210> SEQ ID NO 3
<211> LENGTH: 277
<212> TYPE: PRT
<213> ORGANISM: Homo sapiens
```

```
<400> SEQUENCE: 3

Glu Arg Leu Tyr Lys Pro Val Phe Val Leu Lys Pro Val Ser Phe Lys
 1               5                  10                  15

Cys Leu Glu Gly Ala Asn Cys Arg Phe Asp Leu Lys Val Val Gly Arg
            20                  25                  30

Pro Met Pro Glu Thr Phe Trp Phe His Asp Gly Gln Gln Ile Val Asn
        35                  40                  45

Asp Tyr Thr His Lys Val Val Ile Lys Glu Asp Gly Thr Gln Ser Leu
    50                  55                  60

Ile Ile Val Pro Ala Thr Pro Ser Asp Ser Gly Glu Trp Thr Val Val
65                  70                  75                  80

Ala Gln Asn Arg Ala Gly Arg Ser Ser Ile Ser Val Ile Leu Thr Val
                85                  90                  95

Glu Ala Val Glu His Gln Val Lys Pro Met Phe Val Glu Lys Leu Lys
            100                 105                 110

Asn Val Asn Ile Lys Glu Gly Ser Arg Leu Glu Met Lys Val Arg Ala
        115                 120                 125

Thr Gly Asn Pro Asn Pro Asp Ile Val Trp Leu Lys Asn Ser Asp Ile
    130                 135                 140

Ile Val Pro His Lys Tyr Pro Lys Ile Arg Ile Glu Gly Thr Lys Gly
145                 150                 155                 160

Glu Ala Ala Leu Lys Ile Asp Ser Thr Val Ser Gln Asp Ser Ala Trp
                165                 170                 175

Tyr Thr Ala Thr Ala Ile Asn Lys Ala Gly Arg Asp Thr Thr Arg Cys
            180                 185                 190

Lys Val Asn Val Glu Val Glu Phe Ala Glu Pro Glu Pro Glu Arg Lys
        195                 200                 205

Leu Ile Ile Pro Arg Gly Thr Tyr Arg Ala Lys Glu Ile Ala Ala Pro
    210                 215                 220

Glu Leu Glu Pro Leu His Leu Arg Tyr Gly Gln Glu Gln Trp Glu Glu
225                 230                 235                 240

Gly Asp Leu Tyr Asp Lys Glu Lys Gln Gln Lys Pro Phe Phe Lys Lys
                245                 250                 255

Lys Leu Thr Ser Leu Arg Leu Lys Arg Phe Gly Pro Ala His Phe Glu
            260                 265                 270

Cys Arg Leu Thr Pro
        275

<210> SEQ ID NO 4
<211> LENGTH: 20
<212> TYPE: DNA
<213> ORGANISM: Homo sapiens

<400> SEQUENCE: 4
ggaactacgg gtaagtccct                                              20

<210> SEQ ID NO 5
<211> LENGTH: 20
<212> TYPE: DNA
<213> ORGANISM: Homo sapiens

<400> SEQUENCE: 5 cctttttgaag gaacaatatt                                             20

<210> SEQ ID NO 6
<211> LENGTH: 20
```

-continued

```
<212> TYPE: DNA
<213> ORGANISM: Homo sapiens

<400> SEQUENCE: 6
tggattccaa gtaagtgaat                                                  20

<210> SEQ ID NO 7
<211> LENGTH: 20
<212> TYPE: DNA
<213> ORGANISM: Homo sapiens

<400> SEQUENCE: 7 cttttaaag ctatcaacag                                                   20

<210> SEQ ID NO 8
<211> LENGTH: 20
<212> TYPE: DNA
<213> ORGANISM: Homo sapiens

<400> SEQUENCE: 8
tggaaatcaa gtgggcaaga                                                  20

<210> SEQ ID NO 9
<211> LENGTH: 20
<212> TYPE: DNA
<213> ORGANISM: Homo sapiens

<400> SEQUENCE: 9
ttctctaaag cgtctaacat                                                  20

<210> SEQ ID NO 10
<211> LENGTH: 20
<212> TYPE: DNA
<213> ORGANISM: Homo sapiens

<400> SEQUENCE: 10
agactcgcag gtaagttaaa                                                  20

<210> SEQ ID NO 11
<211> LENGTH: 20
<212> TYPE: DNA
<213> ORGANISM: Homo sapiens

<400> SEQUENCE: 11
taatttcaag caacacaact                                                  20

<210> SEQ ID NO 12
<211> LENGTH: 20
<212> TYPE: DNA
<213> ORGANISM: Homo sapiens

<400> SEQUENCE: 12
cacaagtaag gtaaaaaatt                                                  20

<210> SEQ ID NO 13
<211> LENGTH: 20
<212> TYPE: DNA
<213> ORGANISM: Homo sapiens

<400> SEQUENCE: 13
attcttgtag aagtagatca                                                  20

<210> SEQ ID NO 14
```

-continued

```
<211> LENGTH: 20
<212> TYPE: DNA
<213> ORGANISM: Homo sapiens

<400> SEQUENCE: 14
ggacttcaaa gtaagagaag                                              20

<210> SEQ ID NO 15
<211> LENGTH: 20
<212> TYPE: DNA
<213> ORGANISM: Homo sapiens

<400> SEQUENCE: 15
ttctttctag gtgagtggac                                              20

<210> SEQ ID NO 16
<211> LENGTH: 20
<212> TYPE: DNA
<213> ORGANISM: Homo sapiens

<400> SEQUENCE: 16
gatgtccttg gtaagcctcc                                              20

<210> SEQ ID NO 17
<211> LENGTH: 20
<212> TYPE: DNA
<213> ORGANISM: Homo sapiens

<400> SEQUENCE: 17
taatatatag caaaagaaca                                              20

<210> SEQ ID NO 18
<211> LENGTH: 20
<212> TYPE: DNA
<213> ORGANISM: Homo sapiens

<400> SEQUENCE: 18
accgaataag gtaggatatg                                              20

<210> SEQ ID NO 19
<211> LENGTH: 20
<212> TYPE: DNA
<213> ORGANISM: Homo sapiens

<400> SEQUENCE: 19
tttatttcag cttatatcaa                                              20

<210> SEQ ID NO 20
<211> LENGTH: 20
<212> TYPE: DNA
<213> ORGANISM: Homo sapiens

<400> SEQUENCE: 20
gacgttacgg gtatgtcata                                              20

<210> SEQ ID NO 21
<211> LENGTH: 20
<212> TYPE: DNA
<213> ORGANISM: Homo sapiens

<400> SEQUENCE: 21
tctatttcag cacgtccaaa                                              20
```